United States Patent [19]

Su et al.

[11] Patent Number: 5,091,585
[45] Date of Patent: Feb. 25, 1992

[54] CONTINUOUS PREPARATIN OF TERTIARY ALIPHATIC METHYL AMINES

[75] Inventors: Wei-Yang Su; Robert L. Zimmerman, both of Austin, Tex.

[73] Assignee: Texaco Chemical Company, White Plains, N.Y.

[21] Appl. No.: 631,844

[22] Filed: Dec. 21, 1990

[51] Int. Cl.$^5$ .................. C07C 209/26; C07C 209/24
[52] U.S. Cl. ..................... 564/473; 564/471; 564/472; 564/480
[58] Field of Search .............. 564/473, 472, 471, 480

[56] References Cited

U.S. PATENT DOCUMENTS 4,248,801  2/1981  Tomidokoro et al. .............. 564/463
4,952,734  8/1990  Weber et al. ....................... 564/471

FOREIGN PATENT DOCUMENTS 0142868  5/1985  European Pat. Off. ............ 564/472

Primary Examiner—Glennon H. Hollrah
Assistant Examiner—Shailendra Kumar
Attorney, Agent, or Firm—Jack H. Park; Kenneth R. Priem; David L. Mossman

[57] ABSTRACT

A method for continuous production of tertiary aliphatic methyl amines, particularly fatty aliphatic methyl amines such as di-hydrogenated tallow methyl amine from fatty alkyl amines, such as di-hydrogenated tallow amine over a nickel catalyst has been discovered. The reaction gives high selectivity of tertiary methyl amine over the coproduced secondary amines. The reaction may be conducted continuously in the presence of hydrogen and a formaldehyde source. The formaldehyde source may be selected from the group consisting of formaldehyde alone, formalin, a solution of mixed formaldehyde and paraformaldehyde in methanol and water, trioxane and mixtures thereof. The nickel catalyst may be promoted with copper and/or chromium, in one embodiment.

14 Claims, No Drawings

CONTINUOUS PREPARATIN OF TERTIARY ALIPHATIC METHYL AMINES

FIELD OF THE INVENTION

The invention relates to the production of tertiary aliphatic methyl amines from fatty alkyl secondary amines, and, in one aspect, more particularly relates to the continuous production of tertiary aliphatic methyl amines from fatty alkyl secondary amines using a nickel catalyst.

BACKGROUND OF THE INVENTION

Tertiary aliphatic methyl amines are very useful compounds, finding applications in such various areas as corrosion inhibitors, fuel oil additives, bactericides, fungicides, pigment grinding, ore flotation and as intermediates in the preparation of a wide range of other chemicals, such as quaternary ammonium compounds. Although this versatility has been long known, full utilization of tertiary aliphatic methyl amines has been restricted because of their traditionally high price. Although this disadvantage has been due in part to the cost of the raw materials from which tertiary aliphatic methyl amines are manufactured, the principal cause for their expense has been the lack of commercially acceptable processes for their preparation. There has additionally been no viable means of producing tertiary aliphatic methyl amines by a continuous process which gives good selectivity to the tertiary amines over the co-produced and less valuable secondary and primary by-products. Prior continuous processes also generate catalyst fines which cause reactor plugging problems. To avoid this, prior methods are conducted in batch reactors rather than in continuous systems.

Other known processes for the production of tertiary aliphatic methyl amines includes that described in U.S. Pat. No. 3,136,819. This patent describes a batch process for preparing tertiary aliphatic methyl amines where formaldehyde is progressively added to an amine of the formulae $R_1NH_2$, $(R_1)_2NH$, $R_1R_2NH$ and $R_1NH(CH_2)_3NH_2$, where $R_1$ and $R_2$ represent aliphatic hydrocarbon radicals having from 8 to 22 carbon atoms, maintaining the reactants in the liquid phase under hydrogen pressure at reaction temperature between about 50° and 175° C. and 100-250 psig pressure. The amine contains a hydrogenation catalyst, such as a Raney nickel catalyst. The improvement consisting of employing as an additional catalyst from about 0.5 to about 3 wt. %, based on the amine, of an acid selected from the group consisting of short-chain aliphatic monobasic carboxy, hydroxy monobasic carboxy and dibasic carboxy acids, and benzoic acid. The suitable monobasic acids and hydroxy monobasic acids have at least two carbon atoms, and the dibasic acids have at least three carbon atoms.

U.S. Pat. No. 4,248,801 describes a batch process for making tertiary monomethylamines having long chain alkyl groups from unsaturated aliphatic nitriles under low pressure at high yield by three steps. The first step involves reducing the nitriles with hydrogen in the presence of a nickel hydrogenation catalyst at 200° through 230° C. and under a hydrogen pressure of 0 through 10 kg/cm²G, while the formed ammonia is removed. The second step concerns reacting the resulting amines from the first step with a hydroxymethylation agent in the presence of the nickel catalyst at 150° through 180° C., while hydrogen is passed through the reaction zone under 0.3 through 7 kg/cm²G and the formed water is removed. The last step reduces the resultant tertiary amines with hydrogen in the presence of the nickel catalyst at 175° to 210° C. and under a hydrogen pressure of 5 through kg/cm²G. The patent emphasizes that the third step should not precede the second step.

Of somewhat lesser importance is the three step process described by H. Abe, et al. in "Research on the Synthesis of N,N-di(long-chain alkyl)-methylamines," Yukagaku, Vol. 38, No. 1, (1989) pp. 94–98 (Chemical Abstracts 111:96617r). The article describes the production of tertiary methyl amines from the corresponding alcohol by dehydrogenation, amine addition and hydrogenolysis. The addition of amine (methylamine) proceeds without a catalyst, but copper is a suitable dehydrogenation catalyst and nickel is used as catalyst for the hydrogenolysis. The catalysts may be combined as a copperr-nickel catalyst and used for both steps.

There remains a need for a continuous single-step process for producing tertiary alkyl methyl amines from dialkyl secondary amines simply, and in high selectivities. The batch processes of the patents described above are not believed suitable for adaptation to continuous processes. As noted, the physical stability of prior and current commercial catalysts has been too short and would be expected to cause reactor plugging problems with fines if used to produce commercial quantities of product. Additionally, it is preferred that only one catalyst be used to help reduce process complexity and costs.

SUMMARY OF THE INVENTION

Accrdingly, it is an object of the present invention to provide a process for the continuous production of tertiary alkyl methyl amines, in particular fatty tertiary alkyl methyl amines.

It is another object of the present invention to provide a continuous process for making tertiary alkyl methyl amines that requires only one catalyst.

Another object of the invention is to provide a continuous process for producing tertiary alkyl methyl amines in high selectivity.

In carrying out these and other objects of the invention, there is provided, in one form, a continuous process for the preparation of a tertiary aliphatic methyl amines comprising continuously passing an alkyl secondary amine, hydrogen and a formaldehyde source over a nickel catalyst.

DETAILED DESCRIPTION OF THE INVENTION

It has been discovered that tertiary alkyl methyl amines, particularly fatty tertiary alkyl methyl amines such as di-hydrogenated tallow methyl amine may be produced in high selectivity by passing the corresponding dialkyl secondary amine, such as di-hydrogenated tallow amine, over a nickel catalyst in the presence of hydrogen and a formaldehyde source. This reaction may be schematically illustrated as shown below:

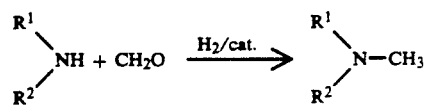

where $R^1$ and $R^2$ are each independently alkyl groups of about 8 to about 22 carbon atoms.

The invention is particularly suited for producing fatty tertiary alkyl methyl amines from secondary alkyl amines which are defined as having from about 8 to about 22 carbon atoms at each alkyl substituent. The product tertiary alkyl methyl amines may have the formula:

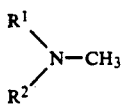

and the reactant secondary alkyl amines may have the formula:

where $R^1$ and $R^2$ are as defined above.

A preferred feedstock because of its relative inexpensiveness is the di-hydrogenated tallow alkyl amine produced from tallow nitrile which has from about 16 to 18 carbon atoms. This material may be made by a number of processes, including, but not limited to the reaction of tallow nitrile over a Co-Zr catalyst described in U.S. patent application Ser. No. 07/506,747, or the reaction of tallow nitrile over a Ni-Cu-Co-Mo catalyst described in U.S. patent application Ser. No. 07/583,110, both incorporated by reference herein. Di-hydrogenated tallow alkyl amine is also available as ARMEEN® 2HT manufactured by Akzo Chemie America.

The formaldehyde source may be any of a number of components. It may include formaldehyde alone, formalin, Methyl Formcel, and trioxane; and mixtures of these. Formalin is a 37 to 50% solution of formaldehyde which may contain 15% methyl alcohol. Methyl Formcel is a 55% by weight solution of mixed monomer and polymer of formaldehyde (paraformaldehyde) in methanol and water. Methyl Formcel a trade name of American Cyanamid. This mixture of formaldehyde and paraformaldehyde in methanol and water is preferred in some embodiments since it was surprisingly discovered that no catalyst fines were produced. The amount of the formaldehyde used in this invention is 1.0 equivalent or more, and preferably, from about 1.0 to about 3.0 equivalent, based on 1.0 equivalent of the starting amine.

The catalyst comprises nickel combinations with one or more transition metals. Transition metals which can be used in conjunction with the nickel include, but are not necessarily limited to manganese, iron, zinc, copper, chromium and mixtures thereof, which act as promoters. In some aspects, a preferred catalyst was obtained where the nickel was combined with copper and chromium.

The quantity of nickel compound and copper or chromium, for example only, employed in the catalyst may vary. The percentage of copper and/or chromium should be from about 2 to about 30 wt. %. From about 70 to about 80 wt. % of nickel in conjunction with from about 20 to 30 wt. % of copper and/or chromium is generally desirable. One preferred catalyst is one described in U.S. Pat. No. 3,152,998, incorporated by reference herein. These catalysts of this invention do not require a support in contrast to prior catalysts.

The reaction is preferably conducted at elevated temperatures and pressures. For example, the temperature may range from about 100° to about 150° C., preferably from about 110° to about 130° C. The pressure may range from about 100 to about 4000 psig, and more preferably range from about 500 to about 3000 psig. It is preferred that hydrogen is present during the reaction.

The reaction is conducted in one continuous stage. The secondary amine, hydrogen and formaldehyde source are all passed continuously over the catalyst. The use of a continuous reaction has advantages over the batch reactions in that no filtration or loss of catalyst is experienced, since a fixed bed is used in the continuous reaction. Running this reaction continuously appears unknown in the art. The invention will be illustrated in greater detail with reference to the following examples.

EXAMPLE 1

To a 550 cc Dowtherm® media heated, stainless steel tubular upward flow reactor was charged 550 cc of a nickel catalyst of this invention containing copper and chromium. Preheated di-hydrogenated tallow alkyl amine (ARMEEN® 2HT, 90.9% secondary amine and 7.5% primary amine) and Methyl Formcel were then run through the reactor bed at 120° C., 2500 psig at a total WHSV (weight hourly space velocity) of 1.0 g/hr-cc. The reactants amine/formaldehyde mole ratio was 1:2, with a 100% excess of hydrogen. The water of the reaction along with the methanol was separated out. An off-white wax product was obtained having an analysis of 93.5% of tertiary amine and 6.5% of secondary amine, as determined by amine analysis and confirmed by NMR analysis. In this and subsequent examples, primary amine was not detected.

EXAMPLE 2

To a 100 cc tubular fixed bed reactor was charged 100 cc of Ni/Cu/Cr catalyst. Preheated di-hydrogenated tallow alkyl amine (ARMEEN 2HT) and formalin were then run through the reactor bed at 120° C., 2500 psig with an amine WHSV of 1.0 g/hr-cc. The reactants amine/formaldehyde mole ratio was 2:5, with a 100% excess of hydrogen. The water of the reaction along with the methanol was separated out. An off-white wax product was obtained having an analysis of 97.2% of tertiary amine and 2.7% of secondary amine.

EXAMPLE 3

The procedure of Example 2 was followed except that the mole ratio of the reactants amine/formaldehyde was 1:2. An off-white wax product was obtained having an analysis of 90.2% of tertiary amine and 9.0% of secondary amine.

EXAMPLE 4

The procedure of Example 2 was followed except that the reaction was carried out at 115° C. An off-white wax product was obtained having an analysis of 97.9% of tertiary amine and 2.1% of secondary amine.

Such excellent results in the continuous production of dihydrogenated tallow methyl amine from di-hydrogenated tallow amine are unknown in the art. Excellent selectivity to the tertiary amine was achieved. Catalyst fines were not found to be a problem, particularly when the mixture of formaldehyde and paraformaldehyde in solution with methanol and water (Methyl Formcel) was used as the formaldehyde source. Many modifications may be made in the process of this invention without departing from the spirit and scope thereof which are defined only in the appended claims. For example, one skilled in the art may discover that particular reaction conditions or sequences, relative flow rates, or catalyst, which may not be explicitly recited herein, but which are nevertheless anticipated, would give desirable results.

We claim:

1. A continuous process for the preparation of a tertiary aliphatic methyl amine comprising continuously passing an alkyl secondary amine, hydrogen and a formaldehyde source over a nickel catalyst promoted with copper and chromium.

2. The process of claim 1 where the formaldehyde source is selected from the group consisting of formaldehyde alone, formalin, a solution of mixed formaldehyde and paraformaldehyde in methanol and water, trioxane and mixtures thereof.

3. The process of claim 1 where the formaldehyde source is a solution of mixed formaldehyde and paraformaldehyde in methanol and water.

4. The process of claim 1 where the formaldehyde source is formalin.

5. The process of claim 1 where the process is carried out at a temperature in the range of about 100° to about 150° C. and a pressure in the range of about 500 to about 4000 psig.

6. The process of claim 5 where the process is carried out at a temperature in the range of about 110° to about 130° C.

7. The process of claim 5 where the process is carried out at a pressure in the range of about 500 to about 3000 psig.

8. The process of claim 1 where the catalyst is at least 70 wt. % nickel and from about 2 to 30 wt. % is treansition metal promoter.

9. The process of claim 1 where the fatty alkyl secondary amine has two fatty alkyl groups, where each group has from 8 to 22 carbon atoms.

10. A continuous process for the preparation of a tertiary aliphatic methyl amine of the fomula:

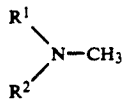

where $R^1$ and $R^2$ are each independently alkyl groups of about 8 to about 22 carbon atoms, comprising continuously passing a fatty alkyl secondary amine of the formula:

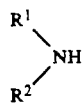

where $R^1$ and $R^2$ are as defined above, over a nickel catalyst promoted with copper and chromium; in the presence of hydrogen and a formaldehyde source, where the formaldehyde source is selected from the group consisting of formaldehyde alone, formalin, a solution of mixed formaldehyde and paraformaldehyde in methanol and water, trioxane and mixtures thereof.

11. The process of claim 10 where the process is carried out at a temperature in the range of about 100° to about 150° C. and a pressure in the range of about 500 to about 4000 psig.

12. The process of claim 10 where the catalyst is at least 70 wt. % nickel and from about 2 to 30 wt. % is transition metal promoter.

13. A continuous process for the preparation of a tertiary aliphatic methyl amine of the formula:

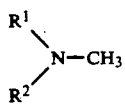

where $R^1$ and $R^2$ are each independently alkyl groups of about 8 to about 22 carbon atoms, comprising continuously passing a fatty alkyl secondary amine of the formula:

where $R^1$ and $R^2$ are as defined above, over a nickel catalyst promoted with copper and chromium, in the presence of hydrogen and a formaldehyde source comprising a solution of mixed formaldehyde and paraformaldehyde in methanol and water, at a temperature in the range of about 100° to about 150° C. and a pressure in the range of about 500 to about 4000 psig, having the advantage that no catalyst fines are produced.

14. The process of claim 13 where the catalyst is at least 70 wt. % nickel and from about 2 to 30 wt. % is transition metal promoter.

* * * * *